(12) United States Patent
Liang

(10) Patent No.: US 11,634,541 B2
(45) Date of Patent: Apr. 25, 2023

(54) CATALYST FOR SYNTHESIZING POLYETHYLENE OXIDE POLYMER AND SYNTHESIS METHOD THEREOF

(71) Applicant: Jiahua Chemicals (Maoming) Co., Ltd., Guangdong (CN)

(72) Inventor: Guoqiang Liang, Guangdong (CN)

( * ) Notice: Subject to any disclaimer, the term of this patent is extended or adjusted under 35 U.S.C. 154(b) by 481 days.

(21) Appl. No.: 16/627,939

(22) PCT Filed: Aug. 17, 2018

(86) PCT No.: PCT/CN2018/101122
§ 371 (c)(1),
(2) Date: Dec. 31, 2019

(87) PCT Pub. No.: WO2019/034150
PCT Pub. Date: Feb. 21, 2019

(65) Prior Publication Data
US 2020/0223982 A1   Jul. 16, 2020

(30) Foreign Application Priority Data

Aug. 18, 2017 (CN) .................. 201710713547.X

(51) Int. Cl.
*C08G 65/26* (2006.01)
(52) U.S. Cl.
CPC ....... *C08G 65/269* (2013.01); *C08G 65/2609* (2013.01); *C08G 65/2612* (2013.01); *C08G 65/2615* (2013.01); *C08G 65/2624* (2013.01); *C08G 65/2648* (2013.01); *C07C 2527/14* (2013.01); *C07C 2531/16* (2013.01); *C07C 2531/22* (2013.01)
(58) Field of Classification Search
CPC .. C08G 65/2642–2693; C07C 2527/14; C07C 2531/00; C07C 2531/16; C07C 2531/22; C07D 323/00
See application file for complete search history.

(56) References Cited

U.S. PATENT DOCUMENTS

| | | | | |
|---|---|---|---|---|
| 4,645,817 A * | 2/1987 | Probst | ................ | C08G 65/2669 528/297 |
| 2007/0173576 A1* | 7/2007 | Desbois | ................ | C08G 65/10 524/167 |
| 2012/0006510 A1* | 1/2012 | Bartelt | .................... | C09K 5/10 165/104.11 |

FOREIGN PATENT DOCUMENTS

| | | |
|---|---|---|
| CN | 102924709 A | 2/2013 |
| CN | 105705551 A | 6/2016 |
| CN | 106905522 A | 6/2017 |
| CN | 107674195 A | 2/2018 |
| EP | 105705551 A1 | 8/2008 |
| JP | 2000256457 A * | 9/2000 |
| WO | 2004041909 A1 | 5/2004 |

OTHER PUBLICATIONS

Czech et al., "Synthesis and Catalytic Activity of a Novel Crown-Quat Phase Transfer Catalyst," Tetrahedron 41, 5439-5444 (1985).*
First Office Action issued in priority CN application 201710713547X, dated Feb. 11, 2019.
Second Office Action issued in priority CN application 201710713547X, dated Jul. 3, 2019.
Decision of Refusal issued in CN application 201710713547X dated Jan. 9, 2020.
International Search Report and Written Opinion, dated Jun. 25, 2019, received in international patent application No. PCT/CN2018/101122, issued Nov. 22, 2018, 13 pages, including English translation.
Jana Herzberger et al: "Polymerization of Ethylene Oxide, Propylene Oxide, and Other Alkylene Oxides: Synthesis, Novel Polymer Architectures, and Bioconjugation", Chemical Reviews, vol. 116, No. 4, Feb. 24, 2016 (Feb. 24, 2016), pp. 2170-2243, XP055266674, US ISSN: 0009-2665, DOI: 10.1021/acs.chemrev.5b00441.
Jurgen Allgaier et al: "Synthesis of Hydrophobic Poly(alkylene oxide)s and Amphiphilic Poly(alkylene oxide) Block Copolymers", Macromolecules, vol. 40, No. 3, Feb. 1, 2007 (Feb. 1, 2007), pp. 518-525, XP055680712, Washington, DC, United States ISSN: 0024-9297, DOI: 10.1021/ma062417g* "... crown ethers and softer counterions such as rubidium, cesium, or different phosphonium ions instead of sodium and potassium were used . . . "; p. 518—right-hand column*.
Zhang Jie et al: "Phosphoniums as catalysts for metal-free polymerization: Synthesis of well-defined poly(propylene oxide)", Journal of Molecular Structure, vol. 1148, May 21, 2017 (May 21, 2017), pp. 421-428, XP085153933, ISSN: 0022-2860, DOI: 10.1016/J. MOLSTRUC.2017.05.094.
Extended European Search Report received in corresponding EP App. No. 18847011.6, dated Jul. 1, 2020.
Third Office Action issued in priority CN application 201710713547X, dated Aug. 4, 2020.

* cited by examiner

Primary Examiner — Kregg T Brooks
(74) Attorney, Agent, or Firm — Verrill Dana, LLP; Robert L. Hover

(57) ABSTRACT

Provided is a catalyst for synthesizing a polyethylene oxide polymer, comprising a crown ether as a first component, a quaternary phosphonium salt as a second component, and an alkali metal and/or an alkali metal compound as a third component. The catalyst can reduce the concentration of alkali metal ions in the product and is suitable for high-standard industrial fields. Also provided is a method for synthesizing a polyethylene oxide polymer, comprising carrying out a reaction of a compound containing active hydrogen and ethylene oxide in the presence of the catalyst. The method is simple to operate and environmentally friendly, improves the quality of the synthesized product, and is suitable for high-standard industrial production.

17 Claims, No Drawings

CATALYST FOR SYNTHESIZING POLYETHYLENE OXIDE POLYMER AND SYNTHESIS METHOD THEREOF

CROSS-REFERENCE TO RELATED APPLICATIONS

This application is a National Stage Entry of International Patent Application No. PCT/CN2018/101122 with an international filing date of Aug. 17, 2018, designating the United States, now pending, and further claims priority benefits to Chinese Patent Application No. 201710713547.X, filed on Aug. 18, 2017. The contents of all of the aforementioned applications are incorporated herein by reference.

TECHNICAL FIELD

The present invention belongs to the technical field of chemical industry, and particularly relates to a catalyst for synthesizing a polyethylene oxide polymer and synthesis method thereof.

BACKGROUND

Polyethylene oxide polymers, such as polyethylene glycol, fatty alcohol polyoxyethylene ether, polyoxyethylene fatty acid, fatty amine polyoxyethylene ether, methoxy polyethylene glycol, allyl alcohol polyoxyethylene ether, isopentenol polyoxyethylene ether or methacryl alcohol polyoxyethylene ether, etc., are considered a significant class of important fine chemical materials, widely used as raw materials in medicine, concrete additives, detergents, textile printing and dyeing auxiliaries, etc. Polyethylene oxide polymer is synthesized through polymerization of a compound containing active hydrogen and ethylene oxide in the presence of a catalyst.

The polymerization of a compound containing active hydrogen and ethylene oxide is usually carried in the presence of an alkaline catalyst such as an alkali metal, alkali metal hydroxide, and alkali metal hydride that are commercially available. The use of an alkaline catalyst can meet the quality and production efficiency of conventional products. However, the products produced by polymerization in the presence of alkali metals or alkali metal hydroxides as catalyst often contain high concentration of residual alkali metal ions, which reduces product quality and environmental protection of product production, limits the application scope of polyethylene oxide polymers in industrial production, and makes the product can not be directly applied to fields such as medicine field where the concentration of metal ions are strictly limited.

SUMMARY OF THE INVENTION

The present invention is designed to solve the problems in the prior art that the polyethylene oxide polymers produced by polymerization in the presence of alkaline catalysts such as alkali metal compounds and alkali metals have a high concentration of residual metal ions, a reduced quality and poor environmental protection, and thus are not suitable for use in high standard industrial production.

In order to solve the above problem, in a first aspect, the present invention provides a catalyst for synthesizing a polyethylene oxide polymer, comprising:
a crown ether as a first component,
a quaternary phosphonium salt as a second component, and
an alkali metal and/or an alkali metal compound as a third component.

Preferably, the quaternary phosphonium salt is selected from the group consisting of methyltriphenylphosphonium bromide, ethyltriphenylphosphonium bromide, propyltriphenylphosphonium bromide, butyltriphenylphosphonium bromide, and any combination thereof, and wherein each component in the combination is present in an amount of 1 to 99 parts by molar.

Preferably, the crown ether is 18-crown (ether)-6, the alkali metal is potassium metal, and the alkali metal compound is potassium hydroxide and/or potassium hydride; or
the crown ether is 15-crown (ether)-5, the alkali metal is sodium metal, and the alkali metal compound is sodium hydroxide and/or sodium hydride; or
the crown ether is 12-crown (ether)-4, the alkali metal is lithium metal, and the alkali metal compound is lithium hydroxide and/or lithium hydride; and
each component in the combination is present in an amount of 1 to 99 parts by molar.

Preferably, a molar ratio of the first component to the second component to the third component is 1:(0.5-1.5):(0.5-1.5).

In a second aspect, the present invention provides a method for synthesizing a polyethylene oxide polymer, comprising the steps of:
(1) preparing a mixture by mixing a compound containing active hydrogen with the above mentioned catalyst and adding ethylene oxide into the mixture under oxygen-free environment or vacuum environment;
(2) carrying out reaction at a temperature of 100° C. to 180° C. and a pressure of less than or equal to 1.0 MPa, followed by aging for 1 h to 8 h to obtain a reaction product comprising a polyethylene oxide polymer; and
(3) adding an acidic compound to the reaction product to neutralize the reaction product.

Preferably, in the method for synthesizing a polyethylene oxide polymer, after the step (2) is completed, an epoxy compound is added to synthesize a polyethylene oxide polymer having a higher molecular weight in the presence of the above catalyst for synthesizing a polyethylene oxide polymer.

Preferably, in the method for synthesizing a polyethylene oxide polymer, prior to adding the propylene oxide into the mixture in the step (1), the mixture is heated to a temperature of 100° C. to 120° C., and then the propylene oxide is added at a temperature of 100° C. to 180° C. and a pressure of less than or equal to 1.0 MPa.

Preferably, in the method for synthesizing a polyethylene oxide polymer, the compound containing active hydrogen is selected from the group consisting of methanol, ethanol, n-butanol, octyl alcohol, natural fatty alcohol, isopentenol, methallyl alcohol, allyl alcohol, 1,4-butene-diol, 2,3-dibromo-1,4-butene-diol, nonylphenol, ethylene glycol, diethylene glycol, glycerol, oleic acid, castor oil, stearic acid, tert-butylamine, fatty amine, and any combination thereof.

Preferably, in the method for synthesizing a polyethylene oxide polymer, a molar ratio of the compound containing active hydrogen to the ethylene oxide is 1:(1-800).

Preferably, in the method for synthesizing a polyethylene oxide polymer, the catalyst is added in an amount of from 0.01% to 0.9% by mass based on a total mass of the compound containing active hydrogen and the ethylene oxide.

The present invention has the following advantages over the prior art:

1. The catalyst for synthesizing a polyethylene oxide polymer provided by the present invention comprises a crown ether as a first component, a quaternary phosphonium salt as a second component, and an alkali metal and/or an alkali metal compound as a third component. The above components of the catalyst cooperate synergistically with each other to ensure the production efficiency, effectively reduce the concentration of metal ions in the produced polyethylene oxide polymer, and improve the quality and environmental friendliness of the produced polyethylene oxide polymer, so that the produced polyethylene oxide polymer is suitable for use in high-standard industrial production.

2. The catalyst for synthesizing a polyethylene oxide polymer provided by the present invention comprises specific crown ethers, quaternary phosphine salts and alkali metals and/or alkali metal compounds at specific ratios. The chosen crown ether, quaternary phosphine salt, and alkali metal and alkali metal compound are easily available, which is helpful to control the production cost. Moreover, due to the specific ratios of the components, the catalyst shows strong catalytic activity.

3. The present invention provides a method for synthesizing a polyethylene oxide polymer, comprising the steps of: preparing a mixture by mixing a compound containing active hydrogen with the above catalyst, and adding ethylene oxide into the mixture under oxygen-free environment or vacuum environment; carrying out reaction at a temperature of 100° C. to 180° C. and a pressure of less than or equal to 1.0 MPa, with a holding time of 1 h to 8 h, to obtain a reaction product comprising a polyethylene oxide polymer; and finally adding an acidic compound to the reaction product to neutralize the reaction product. By using the above catalyst, the environmental friendliness of the production process is improved, and the produced polyethylene oxide polymer has a low metal ion concentration and high quality. The specific reaction temperature and pressure can ensure the catalyst to have high and stable catalytic activity, so that the produced polyethylene oxide polymer has good batch repeatability and stable quality.

4. In the method for synthesizing a polyethylene oxide polymer provided by the present invention, the polyethylene oxide polymer is synthesized at a specific molar ratio of the compound containing active hydrogen to ethylene oxide in the presence of a specific amount of the catalyst, such that the catalyst has high catalytic activity and substrate conversion ability, and that the obtained product has low concentration of metal ions, and that side reactions during the synthesis process are effectively inhibited. The catalyst has good stability, and is suitable for use in a wide temperature range of 100° C. to 180° C. In addition, the method is simple to operate and environmentally friendly, and is suitable for industrial production.

DETAILED DESCRIPTION OF EMBODIMENTS

The implementation of the present invention will be illustrated by the following specific embodiments. Unless otherwise stated, the experimental methods disclosed in the present invention are all based on the conventional technical means in the art, and the reagents and raw materials used in the embodiments are commercially available.

Embodiment 1

Provided is a method for synthesizing a polyethylene oxide polymer, comprising the steps of:

(1) Adding 0.5 mol methallyl alcohol to a high-pressure reactor; and adding 26.5 mol ethylene oxide to a metering tank.

(2) Then adding a catalyst for synthesizing a polyethylene oxide polymer to the reactor in an amount of 0.01% by mass based on a total mass of the methallyl alcohol and the ethylene oxide, wherein the catalyst is composed of 18-crown (ether)-6, potassium the reaction product, producing hydroxide and methyltriphenylphosphonium bromide at a molar ratio of 1:0.5:0.5.

(3) Performing nitrogen replacement after the reactor is closed. Then raising the temperature of the reactor to 100° C. to 120° C., and adding the ethylene oxide from the metering tank to the reactor at this temperature, and continue raising the temperature, and controlling the temperature to be 120° C. to 130° C. and the pressure to be less than or equal to 1.0 MPa.

(4) After the adding of ethylene oxide is completed, closing the feed valve of the ethylene oxide, and holding the temperature at 120° C. to 130° C. and aging for 8 h, producing a reaction product comprising a polyethylene oxide polymer.

(5) Then cooling the temperature of the reactor to 60° C. to 80° C., and adding acetic acid to the reaction product to neutralize the reaction product, producing a polyethylene oxide polymer.

Embodiment 2

Provided is a method for synthesizing a polyethylene oxide polymer, comprising the steps of: (1) Adding 0.5 mol isopentenol to a high-pressure reactor; and adding 25 mol ethylene oxide to a metering tank.

(2) Then adding a catalyst for synthesizing a polyethylene oxide polymer to the reactor in an amount of 0.01% by mass based on a total mass of the isopentenol and the ethylene oxide, wherein the catalyst is composed of 15-crown (ether)-5, sodium hydride and ethyltriphenylphosphonium bromide at a molar ratio of 1:0.8:0.6.

(3) Performing nitrogen replacement after the reactor is closed. Then raising the temperature of the reactor to 100° C. to 120° C., and adding the ethylene oxide from the metering tank to the reactor at this temperature, and continue raising the temperature, and controlling the temperature to be 130° C. to 140° C. and the pressure to be less than or equal to 1.0 MPa.

(4) After the adding of ethylene oxide is completed, closing the feed valve of the ethylene oxide, and holding the temperature at 130° C. to 140° C. and aging for 6 h, producing a reaction product comprising a polyethylene oxide polymer.

(5) Then cooling the temperature of the reactor to 60° C. to 90° C., and adding acetic acid to the reaction product to neutralize the reaction product, producing a polyethylene oxide polymer.

Embodiment 3

Provided is a method for synthesizing a polyethylene oxide polymer, comprising the steps of:

(1) Adding 0.5 mol 1,4-butene-diol to a high-pressure reactor; and adding 32 mol ethylene oxide to a metering tank.

(2) Then adding a catalyst for synthesizing a polyethylene oxide polymer to the reactor in an amount of 0.3% by mass based on a total mass of the 1,4-butene-diol and the ethylene oxide, wherein the catalyst is composed of 12-crown (ether)-4, lithium metal and propyltriphenylphosphonium bromide at a molar ratio of 1:1.1:0.5.

(3) Performing nitrogen replacement after the reactor is closed. Then raising the temperature of the reactor to 100° C. to 120° C., and adding the ethylene oxide from the metering tank to the reactor at this temperature, and continue raising the temperature, and controlling the temperature to be 140° C. to 150° C. and the pressure to be less than or equal to 1.0 MPa.

(4) After the adding of ethylene oxide is completed, closing the feed valve of the ethylene oxide, and holding the temperature at 140° C. to 150° C. and aging for 2 h, producing a reaction product comprising a polyethylene oxide polymer.

(5) Then cooling the temperature of the reactor to 50° C. to 60° C., and adding formic acid to the reaction product to neutralize the reaction product, producing a polyethylene oxide polymer.

Embodiment 4

Provided is a method for synthesizing a polyethylene oxide polymer, comprising the steps of:

(1) Adding 0.5 mol allyl alcohol to a high-pressure reactor; and adding 34 mol ethylene oxide to a metering tank.

(2) Then adding a catalyst for synthesizing a polyethylene oxide polymer to the reactor in an amount of 0.9% by mass based on a total mass of the allyl alcohol and the ethylene oxide, wherein the catalyst comprise a first component, a second component and a third component at a molar ratio of 1:1.5:1.5, and wherein the first component is 18-crown (ether)-6, the second component consists of methyltriphenylphosphonium bromide in an amount of 10 parts by molar, ethyltriphenylphosphonium bromide in an amount of 25 parts by molar, propyltriphenylphosphonium bromide in an amount of 40 parts by molar, and butyltriphenylphosphonium bromide in an amount of 25 parts by molar, and wherein the third component consists of potassium metal in an amount of 15 parts by molar and potassium hydride in an amount of 85 parts by molar.

(3) Performing nitrogen replacement after the reactor is closed. Then raising the temperature of the reactor to 100° C. to 120° C., and adding the ethylene oxide from the metering tank to the reactor at this temperature, and continue raising the temperature, and controlling the temperature to be 100° C. to 110° C. and the pressure to be less than or equal to 1.0 MPa.

(4) After the adding of ethylene oxide is completed, closing the feed valve of the ethylene oxide, and holding the temperature at 100° C. to 110° C. and aging for 8 h, producing a reaction product comprising a polyethylene oxide polymer.

(5) Then cooling the temperature of the reactor to 60° C. to 70° C., and adding formic acid to the reaction product to neutralize the reaction product, producing a polyethylene oxide polymer.

Embodiment 5

Provided is a method for synthesizing a polyethylene oxide polymer, comprising the steps of:

(1) Adding 0.7 mol nonylphenol to a high-pressure reactor; and adding 30 mol ethylene oxide to a metering tank.

(2) Then adding a catalyst for synthesizing a polyethylene oxide polymer to the reactor in an amount of 0.15% by mass based on a total mass of the nonylphenol and the ethylene oxide, wherein the catalyst comprise a first component, a second component and a third component at a molar ratio of 1:1.5:0.5, and wherein the first component is 15-crown (ether)-5, the second component consists of ethyltriphenylphosphonium bromide in an amount of 1 part by molar, propyltriphenylphosphonium bromide in an amount of 50 parts by molar, and butyltriphenylphosphonium bromide in an amount of 49 parts by molar, and wherein the third component consist of sodium metal in an amount of 1 part by molar, sodium hydride in an amount of 30 parts by molar and sodium hydroxide in an amount of 69 parts by molar.

(3) Performing nitrogen replacement after the reactor is closed. Then raising the temperature of the reactor to 100° C. to 120° C., and performing vacuum pumping for 2 h at this temperature, and then adding the ethylene oxide from the metering tank to the reactor, and continue raising the temperature, and controlling the temperature to be 130° C. to 145° C. and the pressure to be less than or equal to 1.0 MPa.

(4) After the adding of ethylene oxide is completed, closing the feed valve of the ethylene oxide, and holding the temperature at 130° C. to 145° C. and aging for 3 h, producing a reaction product comprising a polyethylene oxide polymer.

(5) Then cooling the temperature of the reactor to 70° C. to 80° C., and adding citric acid to the reaction product to neutralize the reaction product, producing a polyethylene oxide polymer.

Embodiment 6

Provided is a method for synthesizing a polyethylene oxide polymer, comprising the steps of:

(1) Adding 0.8 mol octadecylamine to a high-pressure reactor; and adding 25 mol ethylene oxide to a metering tank.

(2) Then adding a catalyst for synthesizing a polyethylene oxide polymer to the reactor in an amount of 0.15% by mass based on a total mass of the octadecylamine and the ethylene oxide, wherein the catalyst comprises a first component, a second component and a third component at a molar ratio of 1:0.8:1.0, and wherein, the first component is 14-crown (ether)-4, the second component is butyltriphenylphosphonium bromide, and the third component consists of lithium metal in an amount of 50 parts by molar and lithium hydroxide in an amount of 50 parts by molar.

(3) Performing nitrogen replacement after the reactor is closed. Then raising the temperature to 100° C. to 120° C., and performing vacuum pumping for 1.5 h at this temperature, and then adding the ethylene oxide from the metering tank to the reactor, and continue raising the temperature, and controlling the temperature to be 160° C. to 170° C. and the pressure to be less than or equal to 1.0 MPa.

(4) After the adding of ethylene oxide is completed, closing the feed valve of the ethylene oxide, and holding the temperature at 160° C. to 170° C. and aging for 3 h, producing a reaction product comprising a polyethylene oxide polymer.

(5) Then cooling the temperature of the reactor to 80° C. to 90° C., and adding phosphoric acid to the reaction product to neutralize the reaction product, producing a polyethylene oxide polymer.

Embodiment 7

Provided is a method for synthesizing a polyethylene oxide polymer, comprising the steps of:

(1) Adding 0.8 mol ethylene glycol to a high-pressure reactor; and adding 25 mol ethylene oxide to a metering tank.

(2) Then adding a catalyst for synthesizing a polyethylene oxide polymer to the reactor in an amount of 0.03% by mass based on a total mass of the ethylene glycol and the ethylene oxide, wherein the catalyst consists of 18-crown (ether)-6, potassium hydride and butyltriphenylphosphonium bromide at a molar ratio of 1:1.0:0.5.

(3) Performing nitrogen replacement after the reactor is closed. Then raising the temperature to 100° C. to 120° C., and adding the ethylene oxide from the metering tank to the reactor, and continue raising the temperature, and controlling the temperature to be 130° C. to 140° C. and the pressure to be less than or equal to 1.0 MPa.

(4) After the adding of ethylene oxide is completed, closing the feed valve of the ethylene oxide, and holding the temperature at 130° C. to 140° C. and aging for 4 h. Then cooling the temperature of the reactor to 40° C. to 50° C., producing a first intermediate product comprising polyethylene oxide polymer and having a molar ratio of ethylene glycol to ethylene oxide of 1:31.25.

(5) Then adding 120 g of the first intermediate product (comprising 0.0834 moles of ethylene glycol and 2.606 moles of ethylene oxide) to the reactor, and adding 27 moles of ethylene oxide to the measuring tank. Then adding a further amount of 0.03% of the catalyst, based on the mass of ethylene oxide. to the reactor.

(6) Performing nitrogen replacement after the reactor is closed. Then raising the temperature to 100° C. to 120° C., and performing vacuum pumping for 1 h at this temperature, and then adding the ethylene oxide from the metering tank to the reactor, and continue raising the temperature, and controlling the temperature to be 140° C. to 150° C. and the pressure to be less than or equal to 1.0 MPa.

(7) After the adding of ethylene oxide is completed, closing the feed valve of the ethylene oxide, and holding the temperature at 140° C. to 150° C. and aging for 6 h. Then cooling the temperature to 70° C. to 80° C., producing a second intermediate product comprising polyethylene oxide polymer and having a molar ratio of ethylene glycol to ethylene oxide of 1:355.

(8) Then adding 1000 g of the first intermediate product (comprising 0.0637 moles of ethylene glycol and 22.6111 moles of ethylene oxide) to the reactor, and adding 28.3489 moles of ethylene oxide to the measuring tank. Then adding a further amount of 0.03% of the catalyst, based on the mass of ethylene oxide, to the reactor.

(9) Performing nitrogen replacement after the reactor is closed. Then raising the temperature of the reactor to 100° C. to 120° C., and performing vacuum pumping for 1 h at this temperature, and then adding the ethylene oxide from the metering tank to the reactor, and continue raising the temperature, and controlling the temperature to be 150° C. to 160° C. and the pressure to be less than or equal to 1.0 MPa.

(10) After the adding of ethylene oxide is completed, closing the feed valve of the ethylene oxide, and holding the temperature at 150° C. to 160° C. and aging for 8 h, producing a reaction product comprising a polyethylene oxide polymer (wherein a molar ratio of ethylene glycol to ethylene oxide is 1:800).

(11) Then cooling the temperature of the reactor to 80° C. to 90° C., and adding acetic acid to the reaction product to neutralize the reaction product, producing a polyethylene oxide polymer, wherein a molar ration of ethylene oxide to ethylene glycol in the raw materials of the polyethylene oxide polymer is 800:1.

Embodiment 8

Provided is a method for synthesizing a polyethylene oxide polymer, comprising the steps of:

(1) Adding 5 mol tetradecanol to a high-pressure reactor; and adding 5 mol ethylene oxide to a metering tank.

(2) Then adding a catalyst for synthesizing a polyethylene oxide polymer to the reactor in an amount of 0.06% by mass based on a total mass of the tetradecanol and the ethylene oxide, wherein the catalyst consists of 15-crown (ether)-5, sodium hydride and butyltriphenylphosphonium bromide at a molar ratio of 1:0.8:0.9.

(3) Performing nitrogen replacement after the reactor is closed. Then raising the temperature to 100° C. to 120° C., and adding the ethylene oxide from the metering tank to the reactor, and continue raising the temperature, and controlling the temperature to be 170° C. to 180° C. and the pressure to be less than or equal to 1.0 MPa.

(4) After the adding of ethylene oxide is completed, closing the feed valve of the ethylene oxide, and holding the temperature at 170° C. to 180° C. and aging for 1 h, providing a reaction product comprising a polyethylene oxide polymer.

(5) Then cooling the temperature to 60° C. to 70° C., and adding acetic acid to the reaction product to neutralize the reaction product, producing a polyethylene oxide polymer.

Embodiment 9

Provided is a method for synthesizing a polyethylene oxide polymer, comprising the steps of:

(1) Adding 0.6 mol oleic acid to a high-pressure reactor; and adding 30 mol ethylene oxide to a metering tank.

(2) Then adding a catalyst for synthesizing a polyethylene oxide polymer to the reactor in an amount of 0.15% by mass based on a total mass of the oleic acid and the ethylene oxide, wherein the catalyst comprises a first component, a second component, and a third component at a molar ratio of 1:0.5:1.5, and wherein, the first component is 18-crown (ether)-6, the second component consists of methyltriphenylphosphonium bromide in an amount of 1 part by molar and ethyltriphenylphosphonium bromide in an amount of 99 parts by molar, and the third component consists of potassium metal in an amount of 1 part by molar and potassium hydroxide in an amount of 99 parts by molar.

(3) Performing nitrogen replacement after the reactor is closed. Then raising the temperature to 120° C., and performing vacuum pumping for 1.5 h at this temperature, and then adding the ethylene oxide from the metering tank to the reactor, and continue raising the temperature, and controlling the temperature to be 170° C. to 180° C. and the pressure to be less than or equal to 1.0 MPa.

(4) After the adding of ethylene oxide is completed, closing feed valve of the ethylene oxide, and holding the temperature at 170° C. to 180° C. and aging for 1 h, producing a reaction product comprising a polyethylene oxide polymer.

(5) Then cooling the temperature of the reactor to 90° C., and adding phosphoric acid to the reaction product to neutralize the reaction product, producing a polyethylene oxide polymer.

Embodiment 10

Provided is a method for synthesizing a polyethylene oxide polymer, comprising the steps of:

(1) Adding 0.7 mol nonylphenol to a high-pressure reactor; and adding 30 mol ethylene oxide to a metering tank.

(2) Then adding a catalyst for synthesizing a polyethylene oxide polymer to the reactor in an amount of 0.15% by mass based on a total mass of the nonylphenol and the ethylene oxide, wherein the catalyst comprises a first component, a second component and a third component at a molar ratio of 1:1.5:0.5, wherein, the first component is 15-crown (ether)-5, the second component consists of ethyltriphenylphosphonium bromide in an amount of 1 part by molar, propyltriphenylphosphonium bromide in an amount of 50 parts by molar, and butyltriphenylphosphonium bromide in an amount of 49 parts by molar, and the third component consists of sodium metal in an amount of 1 part by molar, sodium hydride in an amount of 30 parts by molar, and sodium hydroxide in an amount of 69 parts by molar.

(3) Performing nitrogen replacement after the reactor is closed. Then raising the temperature to 100° C., and performing vacuum pumping for 2 h at this temperature, and then adding the ethylene oxide from the metering tank to the reactor, and continue raising the temperature, and controlling the temperature to be 100° C. to 110° C. and the pressure to be less than or equal to 0.5 MPa.

(4) After the adding of ethylene oxide is completed, closing the feed valve of the ethylene oxide, and holding the temperature at 100° C. to 110° C. and aging for 5 h, producing a reaction product comprising a polyethylene oxide polymer.

(5) Then cooling the temperature of the reactor to 40° C., and adding citric acid to the reaction product to neutralize the reaction product, producing a polyethylene oxide polymer.

Comparative Example 1

Provided is a method for synthesizing a polyethylene oxide polymer, which is the same as that of embodiment 1 except that, in this comparative example, potassium hydroxide is used as a catalyst to replace the catalyst in embodiment 1 in an equal amount.

Comparative Example 2

Provided is a method for synthesizing a polyethylene oxide polymer, which is the same as that of embodiment 2 except that, in this comparative example, sodium hydride is used as a catalyst to replace the catalyst in embodiment 2 in an equal amount.

Comparative Example 3

Provided is a method for synthesizing a polyethylene oxide polymer, which is the same as that of embodiment 3 except that, in this comparative example, lithium metal is used as a catalyst to replace the catalyst in embodiment 3 in an equal amount.

Test Example 1

The concentrations of ethylene oxide in the reactor after the reaction is completed in the embodiments and the comparative examples were measured. The results are shown in Table 1.

TABLE 1

Concentration of alkali metal ions in the reactor after reaction is completed (theoretical calculation)

| | Concentration of alkali metal ions (ppm) |
|---|---|
| Embodiment 1 | 4 |
| Embodiment 2 | 40 |
| Embodiment 3 | 61 |
| Embodiment 4 | 568 |
| Embodiment 5 | 21 |
| Embodiment 6 | 19 |
| Embodiment 7 | 23 |
| Embodiment 8 | 18 |
| Embodiment 9 | 164 |
| Embodiment 10 | 23 |
| Comparative example 1 | 69 |
| Comparative example 2 | 954 |
| Comparative example 3 | 2866 |

Table 1 shows that, the use of a crown ether, an alkali metal and the compound thereof, and a quaternary phosphine salt as a catalyst for synthesizing a polyethylene oxide polymer can effectively convert ethylene oxide to polyethylene oxide polymer, reduce the concentration of residual alkali metal ions after the reaction is completed, and improve the quality of polyethylene oxide polymer products. Compared with using only alkali metals and the compounds thereof as a catalyst, the claimed catalyst comprising a crown ether, an alkali metal and the compound thereof, and a quaternary phosphine salt can significantly low the concentration of the residual alkali metal ions. The method is simple to operate, and the produced product has low concentration of residual alkali metal ions, so the method is environmentally friendly and is suitable for use in high-standard industrial production.

Apparently, the aforementioned embodiments are merely examples illustrated for clearly describing the present invention, rather than limiting the implementation ways thereof. For those skilled in the art, various changes and modifications in other different forms can be made on the basis of the aforementioned description. It is unnecessary and impossible to exhaustively list all the implementation ways herein. However, any obvious changes or modifications derived from the aforementioned description are intended to be embraced within the protection scope of the present invention.

The invention claimed is:

1. A catalyst for synthesizing a polyethylene oxide polymer, comprising:
    a crown ether as a first component,
    a quaternary phosphonium salt as a second component, and
    an alkali metal and/or an alkali metal compound as a third component,
    wherein a molar ratio of the first component to the second component to the third component is 1:(0.5-1.5):(0.5-1.5).

2. The catalyst according to claim 1, characterized in that, the quaternary phosphonium salt is selected from the group consisting of methyltriphenylphosphonium bromide, ethyltriphenylphosphonium bromide, propyltriphenylphosphonium bromide, butyltriphenylphosphonium bromide, and any combination thereof.

3. The catalyst according to claim 1, characterized in that,
the crown ether is 18-crown (ether)-6, the alkali metal is potassium metal, and the alkali metal compound is potassium hydroxide and/or potassium hydride; or
the crown ether is 15-crown (ether)-5, the alkali metal is sodium metal, and the alkali metal compound is sodium hydroxide and/or sodium hydride; or
the crown ether is 12-crown (ether)-4, the alkali metal is lithium metal, and the alkali metal compound is lithium hydroxide and/or lithium hydride.

4. A method for synthesizing a polyethylene oxide polymer, comprising the steps of:
(1) preparing a mixture by mixing a compound containing active hydrogen with the catalyst according to claim 1, and adding ethylene oxide into the mixture under oxygen-free environment or vacuum environment;
(2) carrying out reaction at a temperature of 100° C. to 180° C. and a pressure of less than or equal to 1.0 MPa, followed by aging for 1 h to 8 h to obtain a reaction product comprising a polyethylene oxide polymer; and
(3) adding an acidic compound to the reaction product to neutralize the reaction product.

5. The method according to claim 4, characterized in that, after the step (2) is completed, an epoxy compound is added to synthesize a polyethylene oxide polymer having a higher molecular weight in the presence of the catalyst.

6. The method according to claim 5, wherein the compound containing active hydrogen is selected from the group consisting of methanol, ethanol, n-butanol, octyl alcohol, natural fatty alcohol, isopentenol, methallyl alcohol, allyl alcohol, 1,4-butene-diol, 2,3-dibromo-1,4-butene-diol, nonylphenol, ethylene glycol, diethylene glycol, glycerol, oleic acid, castor oil, stearic acid, tert-butylamine, fatty amine, and any combination thereof.

7. The method according to claim 5, wherein a molar ratio of the compound containing active hydrogen to the ethylene oxide is 1:(1-800).

8. The method according to claim 5, wherein the catalyst is added in an amount of from 0.01% to 0.9% by mass based on a total mass of the compound containing active hydrogen and the ethylene oxide.

9. The method according to claim 4, characterized in that, prior to adding the ethylene oxide into the mixture in the step (1), the mixture is heated to a temperature of 100° C. to 120° C., and then the ethylene oxide is added at a temperature of 100° C. to 180° C. and a pressure of less than or equal to 1.0 MPa.

10. The method according to claim 9, wherein the compound containing active hydrogen is selected from the group consisting of methanol, ethanol, n-butanol, octyl alcohol, natural fatty alcohol, isopentenol, methallyl alcohol, allyl alcohol, 1,4-butene-diol, 2,3-dibromo-1,4-butene-diol, nonylphenol, ethylene glycol, diethylene glycol, glycerol, oleic acid, castor oil, stearic acid, tert-butylamine, fatty amine, and any combination thereof.

11. The method according to claim 9, wherein a molar ratio of the compound containing active hydrogen to the ethylene oxide is 1:(1-800).

12. The method according to claim 9, wherein the catalyst is added in an amount of from 0.01% to 0.9% by mass based on a total mass of the compound containing active hydrogen and the ethylene oxide.

13. The method according to claim 4, characterized in that, the compound containing active hydrogen is selected from the group consisting of methanol, ethanol, n-butanol, octyl alcohol, natural fatty alcohol, isopentenol, methallyl alcohol, allyl alcohol, 1,4-butene-diol, 2,3-dibromo-1,4-butene-diol, nonylphenol, ethylene glycol, diethylene glycol, glycerol, oleic acid, castor oil, stearic acid, tert-butylamine, fatty amine, and any combination thereof.

14. The method according to claim 13, wherein a molar ratio of the compound containing active hydrogen to the ethylene oxide is 1:(1-800).

15. The method according to claim 13, wherein the catalyst is added in an amount of from 0.01% to 0.9% by mass based on a total mass of the compound containing active hydrogen and the ethylene oxide.

16. The method according to claim 4, characterized in that, a molar ratio of the compound containing active hydrogen to the ethylene oxide is 1:(1-800).

17. The method according to claim 4, characterized in that, the catalyst is added in an amount of from 0.01% to 0.9% by mass based on a total mass of the compound containing active hydrogen and the ethylene oxide.

* * * * *